United States Patent
Saito et al.

(10) Patent No.: US 8,937,204 B1
(45) Date of Patent: Jan. 20, 2015

(54) PROCESSES FOR ISOLATING FLUORINATED PRODUCTS

(71) Applicant: UBE Industries, Ltd., Yamaguchi (JP)

(72) Inventors: Norimichi Saito, Denver, CO (US); Junichi Chika, Denver, CO (US); Teruo Umemoto, Denver, CA (US)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 14/370,699

(22) PCT Filed: Feb. 7, 2013

(86) PCT No.: PCT/JP2013/053595
§ 371 (c)(1),
(2) Date: Jul. 3, 2014

(87) PCT Pub. No.: WO2013/118915
PCT Pub. Date: Aug. 15, 2013

Related U.S. Application Data

(60) Provisional application No. 61/597,056, filed on Feb. 9, 2012.

(51) Int. Cl.
*C07C 17/02* (2006.01)
*C07C 17/38* (2006.01)
*C07C 313/00* (2006.01)
*C07C 17/395* (2006.01)

(52) U.S. Cl.
CPC .................................. *C07C 17/395* (2013.01)
USPC .............................. 570/219; 570/211; 558/61

(58) Field of Classification Search
USPC ...................... 570/219, 211; 558/61
See application file for complete search history.

(56) References Cited

PUBLICATIONS

Singh et al., deoxofluorination of 4-hydroxyproline derivative using 4-tert-butyl-2,6-dimethylphenylsulfur trifluoride (Journal of organic chemistry vol. 76, No. 9 (2011) pp. 3113-3121).*

* cited by examiner

*Primary Examiner* — Jafar Parsa
(74) *Attorney, Agent, or Firm* — Swanson & Bratschun, L.L.C.

(57) ABSTRACT

Useful processes for isolating the fluorinated products formed by reaction with 4-tert-butyl-2,6-dimethylphenylsulfur trifluoride (Fluolead) are disclosed. The processes comprise the conversion of the byproduct (formula I) to sulfinate ester (formula V), and to sulfonate eater (formula VI), and then to the water-soluble sulfonate salt (formula IV) in the presence of the fluorinated products.

5 Claims, No Drawings

PROCESSES FOR ISOLATING FLUORINATED PRODUCTS

RELATED APPLICATIONS

This application is a 35 U.S.C. §371 national phase application of International Application Serial No. PCT/JP2013/053595, filed Feb. 7, 2013 (WO 2013/118915). International Application Serial No. PCT/JP2013/053595 claims the benefit of U.S. Provisional Application Ser. No. 61/597,056, filed Feb. 9, 2012, which is incorporated herein by reference in its entirety.

TECHNICAL FIELD

The invention relates to processes for isolation of fluorinated products from byproducts where the fluorination products are prepared using 4-tert-butyl-2,6-dimethylphenylsulfur trifluoride (Fluolead).

BACKGROUND ART

The present invention relates to processes for isolating fluorinated products in fluorination reactions that utilize 4-tert-butyl-2,6-dimethylphenylsulfur trifluorides (Fluolead). Fluolead has recently been developed as a very useful deoxofluorinating agent with high thermal stability, ease of handling, unusual resistance to aqueous hydrolysis, and wide application [see, for example, J. Am. Chem. Soc., 2010, 132, 18199-18205 and its supporting information]. Fluolead's excellent and unique properties are based on extremely high lipophilicity caused by a tert-butyl and two methyl substituents on a benzene ring. Fluolead fluorinates many kinds of organic compounds such as alcohols, aldehydes, ketones, carboxylic acids, thioketones, thioesters, dithioesters, thiocarbonate, and dithiocarbonates to give the corresponding fluorinated compounds in high yields. These fluorinated compounds are useful for the preparation or development of medicines, agrochemicals, liquid crystals, and the like (see, for example, J. Fluorine Chem. 2006, Vol. 127, pp. 992-1012; Chem. & Eng. News, June 5, pp. 15-32 (2006); "Modern Fluoroorganic Chemistry—Synthesis, Reactivity, Applications", Wily-VCH, Weinheim (2004), pp. 203-277; Angew. Chem. Ind. Ed., Vol. 39, pp. 4216-4235 (2000)). Therefore, Fluolead has high potential to apply to these industries due to its high fluorination capability.

However, there is a drawback in fluorination reactions using Fluolead. Fluolead reacts with an organic compound to form an equimolar amount of a byproduct, 4-tert-butyl-2,6-dimethylphenylsulfinyl fluoride (represented by compound (I)), along with the fluorinated product. The byproduct is difficult to separate from the fluorinated product and results in a loss of product purity and therefore product effectiveness (see equation 1 for reaction overview).

[Equation 1]

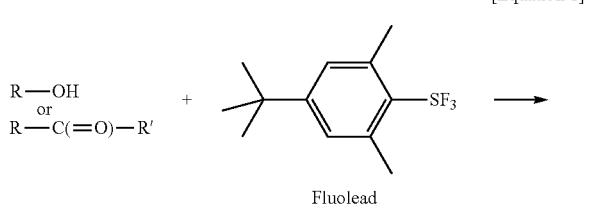

Fluolead

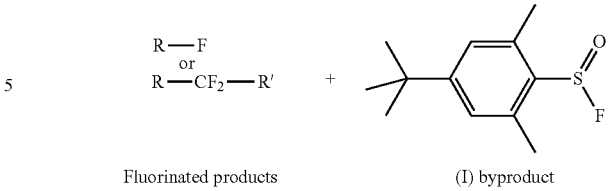

Fluorinated products  (I) byproduct

The byproduct (I) cannot be removed from the organic layer of the reaction mixture by washing it with an aqueous alkaline solution (a required step in the isolation of the fluorinated products), because the byproduct (I) undergoes a disproportionation reaction during hydrolysis to substantially form thiolsulfonate (compound (III)) and sulfonate salt (compound (IV)), as shown in the following scheme 1:

Scheme 1

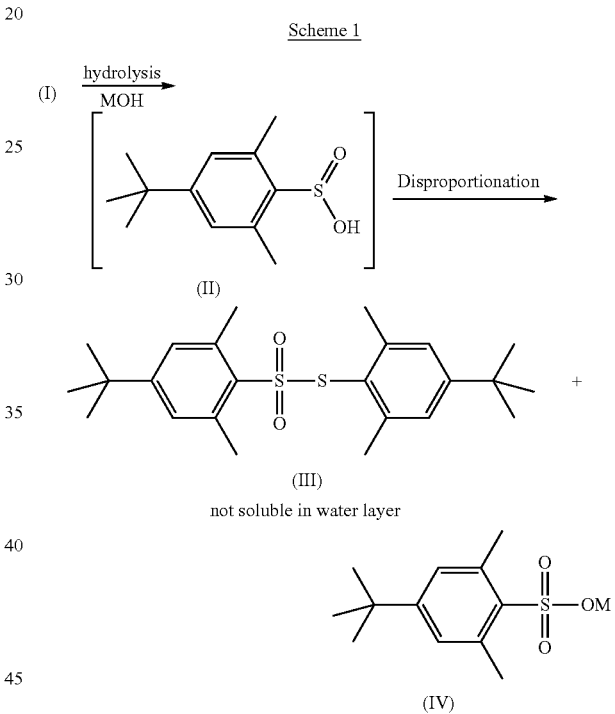

Although compound (IV) is soluble in an aqueous layer, compound (III) is not. Therefore, the fluorinated products cannot be separated from byproduct (III). The extraordinary easy occurrence of the disproportionation of byproduct (I) to (III) via (II) is owing to its high lipophilicity caused by its unique chemical structure, that is, one tert-butyl and two methyl substituents on a benzene ring. Therefore, the fluorinated compounds are contaminated with a significant amount of solid thiolsulfonate (III). Column-chromatography for the separation of compound (III) from the fluorinated products requires is relatively costly, and is not suitable for the large scale production. Alternatively, fractional distillation for the separation has limited scope, because it cannot be applied to solid fluorinated products. Therefore, the solution to producing industrial amounts of fluorinated products using Fluolead requires a new approach.

The present invention is directed toward overcoming the problem discussed above.

SUMMARY OF INVENTION

The present invention provides processes for effective isolation of a fluorinated product(s) from byproducts during fluorination reactions using 4-tert-butyl-2,6-dimethylphenylsulfur trifluoride (Fluolead). The processes comprise converting the byproducts of the reaction, represented by compound (I), to water-soluble sulfonate salts, having a formula of compound (IV). The sulfonate salts being removed from the fluorinated products via solubility differences between the two groups of materials, i.e., sulfonate salts being soluble in the aqueous layer and the fluorinated products in the organic layer. These processes are extremely effective at removing substantially all of the byproduct from the fluorinated product and thereby providing an unexpectedly useful and pure fluorinated product. In alternative embodiments, other differences in physical properties between the sulfonate salts and fluorinated products can be used for separation, for example, differences in their ionic and non-ionic natures.

The present invention provides methods for converting byproduct (I) to sulfinate ester of formula (V), and then to sulfonate ester of formula (VI), and then to sulfonate salt of formula (IV) in the presence of a fluorinated product formed in the fluorination with Fluolead.

The present invention also provides methods which comprise a first step of treating a mixture of a fluorinated product and byproduct (I) with an alcohol, a second step of treating a mixture of the fluorinated product and sulfinate ester (V) with an oxidizer, and a third step of treating the fluorinated product and sulfonate ester (VI) with a nucleophile. Note that two steps (steps one and two, or steps two and three) can also be performed at substantially the same time. All the steps (steps one, two, and three) may also be performed at substantially the same time.

The fluorinated product is isolated by simple processes of the present invention that are very cost effective. This method is quite suitable for large scale production as it is based on the physical properties differences between the fluorinated products and the ionic sulfonate salt compound.

These and various other features as well as advantages which characterize the invention will be apparent from a reading of the following detailed description and a review of the appended claims.

DESCRIPTION OF EMBODIMENT

Embodiments of the present invention provide processes for isolation of fluorinated products in fluorination reactions using 4-tert-butyl-2,6-dimethylphenylsulfur trifluoride (Fluolead). These processes are useful at an industrial scale, providing fluorinated products of high yield and high purity. The byproducts are very effectively, safely, and at low cost removed from the fluorinated products. The separation of substantially all byproduct from the fluorinated product relies on the conversion of the byproduct to a corresponding sulfonate salt. The physical differences (physical property differences) between the neutral byproduct and the ionic sulfonate salt are utilized to separate the salt away from the fluorinated product (differences not present between the byproduct and fluorinated products). In one embodiment, the physical differences can be realized via liquid-liquid or liquid-solid extraction principles which allow for use in industrial scale application. Alternative embodiments can utilize absorption characteristics of the sulfonate salt against the fluorinated products.

The present invention provides methods comprising: in the presence of a fluorinated product, a byproduct having a formula (I) is converted to a water-soluble sulfonate salt having a formula (IV).

In more detail, the present invention provides methods which comprise converting the byproduct (I) to sulfinate ester having a formula (V), and then to sulfonate ester having a formula (VI), and then to the sulfonate salt having a formula (IV). The compounds (I), (V), (VI), and (IV) are as follows:

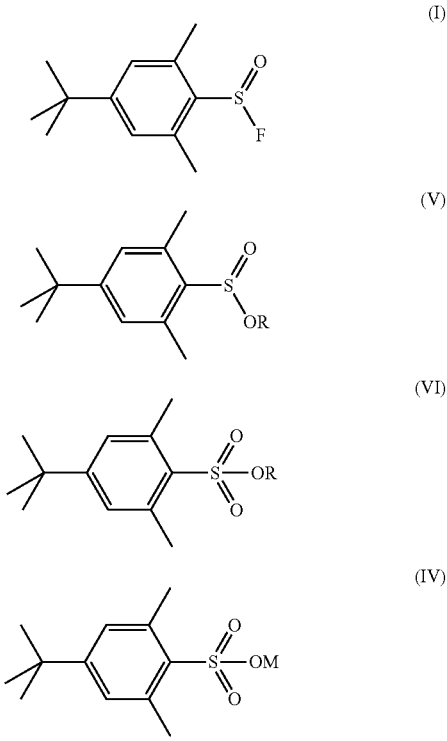

in which: R is alkyl group having 1 to 4 carbon atoms and M is a hydrogen atom, a metal atom, or an ammonium moiety.

The present invention may include three steps for the conversion of byproduct (I) to sulfonate salt (IV), as shown in the following equation (Equation 2):

[Equation 2]

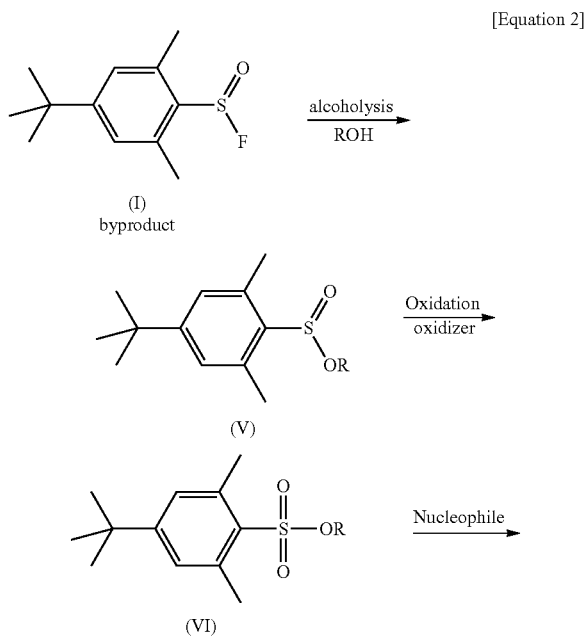

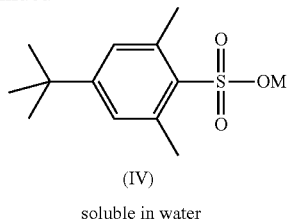

(IV)

soluble in water

In one embodiment, the three steps are (step 1) alcoholysis step, (step 2) oxidation step, and (step 3) nucleophile treatment step, and this three-steps procedure may be followed by the first fluorination reaction of an organic compound with Fluolead (see, Scheme 2).

Scheme 2: (Steps 1, 2, and 3)

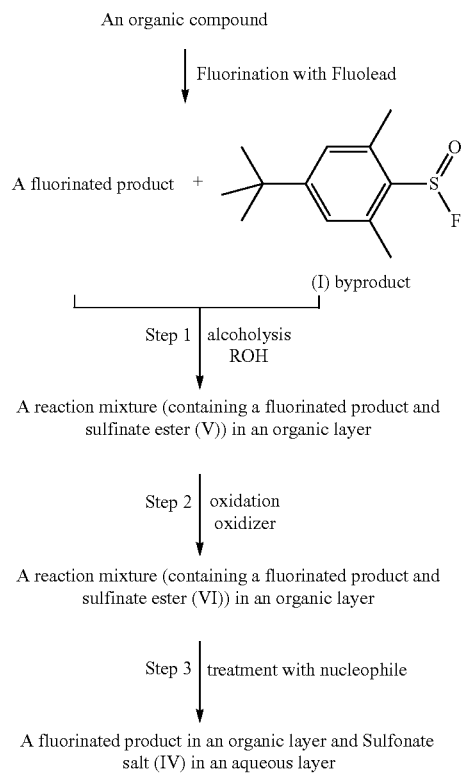

Step 1 in Scheme 2

Step 1 is a process for treating a mixture with alcohol. The mixture is obtained from fluorination reaction of an organic compound with 4-tert-butyl-2,6-dimethylphenylsulfur trifluoride (Fluolead) and the mixture includes a fluorinated product and byproduct as represented by formula (I).

Fluolead is commercially available. The organic compounds fluorinated with Fluolead are exemplified as any organic compounds which are fluorinated with Fluolead. Typically, the organic compounds are selected from a group consisting of alcohols, aldehydes, ketones, diketones, keto esters, carboxylic acids, thioketones, thioesters, dithioesters, thiocarbonates, and dithiocarbonates. The fluorination of organic compounds with Fluolead can be carried out according to the known reaction procedures and conditions (see, for example, *J. Am. Chem. Soc.*, 2010, 132, 18199-18205 and tis supporting information, incorporated herein by reference for all purposes).

Step 1 comprises treating the obtained mixture with an alcohol.

The mixture used for step 1 contains a fluorinated product(s) and byproduct (I). In addition, the mixture may contain Fluolead and/or the non-fluorinated organic compound, which are unreacted or overused in the fluorination process with Fluolead. Fluolead reacts with an alcohol to quantitatively give sulfinate ester of formula (V).

The alcohols used for this step can be selected from the group including: methanol, ethanol, propanol, isopropanol, butanol, isobutanol, sec-butanol, and tert-butanol. Among them, methanol and ethanol are preferable because of their availability and cost.

Step 1 can be accomplished by adding a suitable amount of alcohol to the reaction mixture and the resulting mixture is stirred until byproduct (I) is completely converted to sulfinate ester (V).

In order to get an excellent conversion of compounds represented by formula (I) to compounds represented by formula (V), a preferable amount of alcohol can be chosen in the range of about 1 mol to a large excess per 1 mol of the byproduct (I). About 3 mol to about 20 mol of alcohol is more preferable per 1 mol byproduct. The alcohol can also be used as a solvent or one of solvents for this step (step 1). The amount of byproduct can be predicted via the expected yield of the fluorinated products produced by Fluolead (the byproduct is formed in at least equimolar amount to the fluorinated product) or via objective detection standards like NMR or the like. The amount of byproduct may be evaluated by the amount of Fluolead that was originally used.

When unreacted or overused Fluolead is included in the mixture, an additional amount of alcohol is needed, which reacts with all the Fluolead to form sulfinate ester of formula (V). In order to convert Fluolead to the sulfinate, a preferable amount of alcohol is about 3 mol to about 20 mol per 1 mol of Fluolead. A large excess of alcohol can also be used.

In order to get an excellent conversion of compound (I) to compound (V), the reaction temperature is in the range of about $-20°$ C.$\sim+100°$ C. More preferably, the reaction temperature is about $0°$ C.$\sim+50°$ C.

The reaction time can be chosen to complete the conversion. Typically, it is within a day, and more preferable within several hours.

The reaction of Step 1 is carried out with or without any other solvent. Suitable solvents for use herein include, but are not limited to, alkanes, halocarbons, aromatics, ethers, nitriles and so on, as well as mixtures of the above. Illustrative alkanes are normal, branched, or cyclic pentane, hexane, heptane, octane, nonane, decane, and so on. Illustrative halocarbons are dichloromethane, chloroform, carbon tetrachloride, dichloroethane, trichlorotrifluoroethane, and so on. Illustrative aromatics are benzene, toluene, xylene, chlorobenzene, fluorobenzene, benzotrifluoride, and so on. Illustrative ethers are diethyl ether, dipropyl ether, di(isopropyl)ether, dibutyl ether, tert-butyl methyl ether, tetrahydrofuran, dioxane, methyl nonafluorobutyl ether, ethyl 1,1,2,2-tetrafluoroethyl ether, 1,1,2,2-tetrafluoroethyl 2,2,2-trifluoroethyl ether, and so on. Illustrative nitriles are acetonitrile, propionitrile, butyronitrile, and so on. As noted above, an alcohol as a reactant for this step can also be used as a solvent or one of solvents.

Note that because, in many cases, solvent is already in the Fluolead reaction to produce fluorinated products, additional solvent is often not required, i.e., the solvent from the original reaction is present and all that needs to be added is the alcohol. However, additional solvent can be added to the reaction, even where the original reaction included solvent.

Step 2 in Scheme 2

Step 2 is a process of treating the reaction mixture obtained from step 1 with an oxidizer. The reaction mixture for step 2 includes the fluorinated product and sulfinate ester of formula (V). The oxidizer can be selected from normal oxidizers such as hydrogen peroxide, hydroge peroxide-urea adduct, peracetic acid, perbenzoic acid, m-chloroperbenzoic acid, monoperoxy oxalic acid, monoperphthalic acid, nitric acid, potassium peroxymonosulfate (Oxone$^R$), sodiun perchlorate, sodium perbromate, sodium periodate, potassium periodate, sodium persulfate, potasium permanganate, sodium perborate, sodium percarbonate, bromine, chlorine, sodium hypochlorite, and the like.

In order to get significant conversion of compound (V) to compound (VI), a preferable amount of an oxidizer can be chosen in the range of about 1 mol to about 5 mol per 1 mol of the sulfinate ester (amount of sulfinate ester evaluated by determining how much byproduct was originally present, or how much Fluolead was originally used, for example). About 1 mol to about 3 mol of oxidizer is more preferable.

In order to get significant conversion of compound (V) to compound (VI), the reaction temperature is in the range of about −20° C.∼+120° C. More preferably, the reaction temperature is about 0° C.∼+100° C.

The reaction time can be chosen to complete the conversion. Typically, it is within a few days, and more preferable within a day.

The reaction of step 2 is carried out with or without any other solvent. The use of the solvent is preferable for mild reaction conditions. Suitable solvents for use herein include, but are not limited to, water, alcohols, carboxylic acids, alkanes, halocarbons, aromatics, ethers, and so on, as well as mixtures of the above. Illustrative alcohols include, but are not limited to, methanol, ethanol, propanol, isopropanol, butanol, and so on. Illustrative carboxylic acids are formic acid, acetic acid, propionic acid, and so on. Alkanes, halocarbons, aromatics, and ethers are exemplified as for step 1. As above the original solvent used in step 1 can be used for step 2. Additional solvent can be added in step 2 if necessary. Note also that the solvent used in step 1 and used in 2 do not have to be the same, for example an alcohol could be used in step 1 and a carboxylic acid used in step 2. Because step 2 is an oxidation reaction, solvents must allow for the oxidation step. Addition of solvent to step 2 can be determined for making the reaction smooth, i.e., accomplish the reaction in a pre-set amount of time (in some instances the progress of the reaction can be checked using gas chromatography or other like methodologies).

Step 3 in Scheme 2

Step 3 is treating the reaction mixture obtained from step 2 with a nucleophile to convert sulfonate ester of formula (VI) to sulfonate salt of formula (IV) which is soluble in water or alkaline water. The reaction mixture includes the fluorinated product and sulfonate ester of formula (VI). The nucleophiles used in step 3 includes, are not limited to, water, hydroxides, alkoxides, amines, halides, cyanides, and so on. Illustrative hydroxides include lithium hydroxide, sodium hydroxide, potassium hydroxide, and so on. Illustrative alkoxides includes lithium methoxide, sodium methoxide, potassium methoxide, lithium ethoxide, sodium ethoxide, potassium ethoxide, and so on. Illustrative amines includes ammonia, methylamine, dimethylamine, ethylamine, diethylamine, propylamine, dipropylamine, and so on. Illustrative halides include sodium chloride, potassium chloride, sodium bromide, potassium bromide, sodium iodide, potassium iodide, and so on. Illustrative cyanides include sodium cyanide, potassium cyanide, and so on. Between these sodium and potassium compounds, potassium compounds are preferable because potassium 4-tert-butyl-2,6-dimethylphenylsulfonate (IV: M=K) is more soluble in water than sodium 4-tert-butyl-2,6-dimethylphenylsulfonate (IV: M=Na).

In order to get an excellent conversion of compounds represented by formula (VI) to compounds represented by formula (IV), a preferable amount of a nucleophile can be chosen in the range of about 1 mol to a large excess per 1 mol of the sulfonate ester. About 1 mol to about 10 mol of a nucleophile is preferable.

In order to get an excellent conversion of compounds of (VI) to compounds of (IV), the reaction temperature is in the range of about −20° C.∼+120° C. More preferably, the reaction temperature is about 0° C.∼+100° C.

The reaction time can be chosen to complete the conversion. Typically, it is within a few days, and more preferable within a day.

The reaction of step 3 is carried out with or without any other solvent. The use of the solvent is preferable for mild reaction conditions and high yield reaction. Suitable solvents for use herein include, but are not limited to, water, alcohols, ether, and so on, as well as mixtures of the above. Illustrative alcohols include, but are not limited to, methanol, ethanol, propanol, isopropanol, butanol, and so on. Illustrative ethers are diethyl ether, dipropyl ether, di(isopropyl)ether, dibutyl ether, tert-butyl methyl ether, tetrahydrofuran, dioxane, and so on. The solvent used for the step 2 can be used for step 3.

A distinction from processes in the prior art is that embodiments of the invention utilize simple techniques suitable for the large scale production of fluorinated products. These processes can utilize, for example, liquid-liquid or liquid-solid extraction techniques, where the sulfonate salt is separated away from the fluorination products as shown in Scheme 2.

According to the present invention, the fluorinated products can be isolated by means of standard simple processes which do not require column chromatography, fine distillation purification, and any other special performance of high technology. This is a significant improvement in industrial application over the prior art to isolate the fluorinated products.

The following examples will illustrate the present invention in more detail, but it should be understood that the present invention is not deemed to be limited thereto.

EXAMPLES

Example 1

Isolation of 2,7-dibromo-9,9-difluorofluorene formed in the fluorination of 2,7-dibromo-9-fluorenone with Fluolead

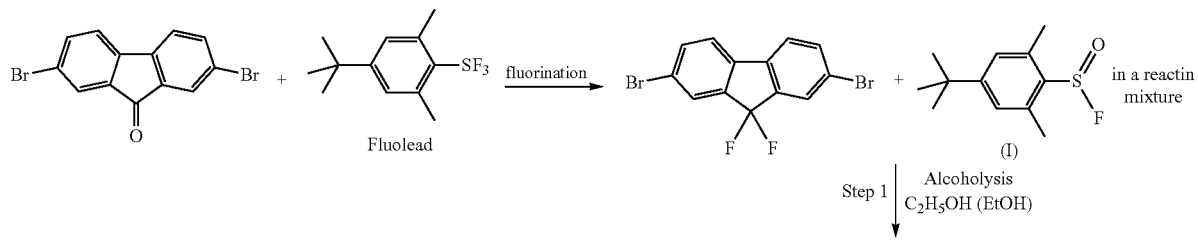

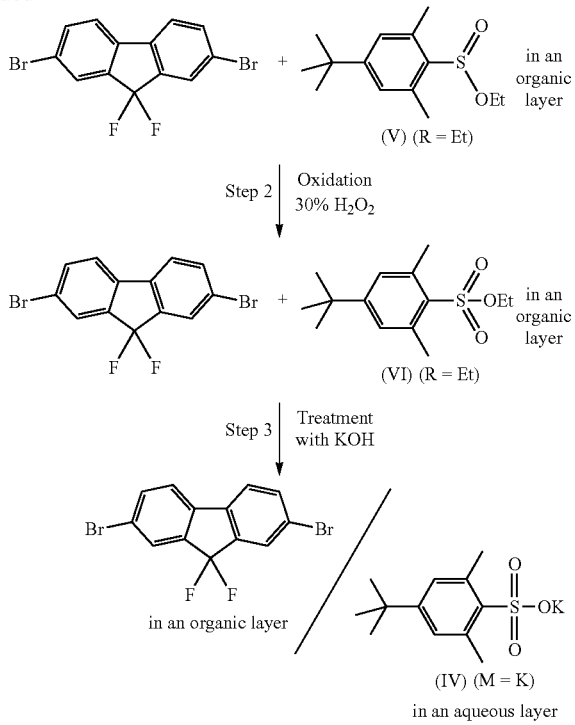

A fluoropolymer (PFA) reactor with septum/port was charged with 13.5 g (40 mmol) of 2,7-dibromo-9-fluorenone, 21.7 g (80 mmol) of 4-tert-butyl-2,6-dimethylphenylsulfur trifluoride (purity 93%) (Fluolead), 40 mL of dry toluene, and 4.0 mL of a 7:3 (wt/wt) mixture of hydrogen fluoride and pyridine. The reactor was closed with septum and placed in an oil bath at 77° C. for 24 hrs.

(Step 1): After cooling in an ice bath, 30 mL of ethanol was added to the reaction mixture. The ice bath was removed and reaction mixture was stirred for 30 minutes, after which it was poured into an aqueous solution of 40 g of sodium carbonate in 500 mL of water. The organic layer was separated and the aqueous layer was extracted with ether. The combined organic layer was washed with water, dried with sodiun sulfate, and filtered. The filtrate was evaporated to give 38.93 g of a residue, which has the fluorinated product and ethyl 4-tert-butyl-2,6-dimethylphenylsulfinate (V) (R=Et) by GC analysis and NMR analysis. Spectral data of ethyl 4-tert-butyl-2,6-dimethylphenylsulfinate: $^1$H NMR (CDCl$_3$) δ 7.03 (s, 2H), 4.15 (m, 2H), 2.62 (s, 6H), 1.38 (t, J=7 Hz, 3H), 1.28 (s, 9H); GC-Mass 254 (M$^+$).

(Step 2): The residue was then dissolved in 80 mL of acetic acid. The mixture was heated in an oil bath at 70° C. and then 13.6 g of 30% hydrogen peroxide (H$_2$O$_2$, 0.12 mol) was added in portions over 15 minutes. The mixture was stirred for additional 2 hrs, cooled to room temperature, and then poured into water including 16 g of sodiun sulfite. The mixture was extracted with a mixture of toluene and ether and the organic layer was washed with water, dried with sodium sulfate, and filtered. The filtrate was evaporated to give 23.03 g of a residue, which has the fluorinated compound and ethyl 4-tert-butyl-2,6-dimethylphenylsulfonate (VI) (R=Et) by GC and NMR analysis. Spectral data of ethyl 4-tert-butyl-2,6-dimethylphenylsulfonate: $^1$H NMR (CDCl$_3$) δ 7.14 (s, 2H), 4.07 (quartet, J=7.1 Hz, 2H), 2.66 (s, 6H), 1.32 (t, J=7.1 Hz, 3H), 1.30 (s, 9H); GC-Mass 270 (M$^+$).

(Step 3): The residue was mixed with 100 mL of ethanol and the mixture was heated at 70° C. Into the mixture, 20 mL of 10% KOH aqueous solution was added and the mixture was stirred for 2 hrs at 70° C. After cooling to room temperature, the mixture was concentrated and the resulting mixture was mixed with water and extracted with ether. The combined organic layer was washed with water, dried with sodium sulfate, and filtered. Solvent of the filtrate was removed to give 16.45 g of a yellow solid residue which is the fluorinated product by GC analysis. The GC analysis showed the yellow solid residue did not include any of ethyl 4-tert-butyl-2,6-dimethylphenylsulfonate. The solid residue was triturated in 25 mL of ethanol, chilled in an ice bath, and then filtered to give 13.3 g of the fluorinated product, 2,7-dibromo-9,9-difluorofluorene after drying. The product's yield was 92% and purity was 100% by GC analysis.

Spectral data of 2,7-dibromo-9,9-difluorofluorene: $^1$H NMR (CDCl$_3$) δ 7.73 (broad quartet, J=1.6 Hz, 1H), 7.58 (dd, J=8.1 Hz, 0.7 Hz, 1H), 7.37 (d, J=8.1 Hz, 1H); $^{19}$F NMR (CDCl$_3$) δ −110.87 (s); GC-Mass 362 (M$^+$), 360 (M$^+$), 358 (M$^+$).

While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims. All publications cited herein are hereby incorporated by reference.

The invention claimed is:

1. A method for isolating a fluorinated product from a byproduct where the fluorinated product results from fluorination with 4-tert-butyl-2,6-dimethylphenylsulfur trifluoride:

the method comprising:
in the presence of the fluorinated product, converting the byproduct having a formula (I) to a sulfinate ester having a formula (V), and then to a sulfonate ester having a formula (VI), and then to a sulfonate salt having a formula (IV);

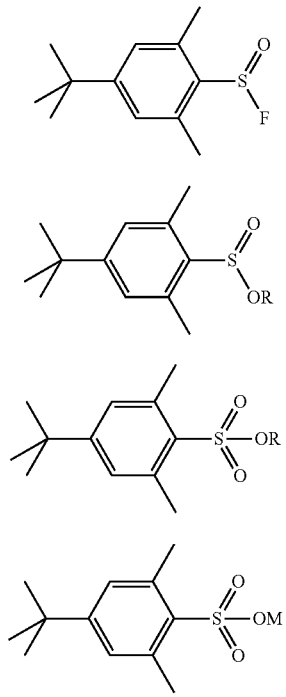

in which: R is alkyl group having 1 to 4 carbon atoms and M is a hydrogen atom, a metal atom or an ammonium moiety;

and wherein the fluorinated product is isolated from the byproduct by utilizing physical property differences between the byproduct and sulfonate salt.

2. The method of claim 1 which comprises:

a first step of treating a mixture including the fluorinated product and the byproduct (I) with an alcohol to convert (I) to sulfinate ester (V);

a second step of treating a mixture including the fluorinated product and the sulfinate ester (V) obtained in the first step with an oxidizer to convert (V) to sulfonate ester (VI):

and a third step of treating a mixture including the fluorinated product and the sulfonate ester (VI) obtained in the second step with a nucleophile to convert (VI) to sulfonate salt (IV).

3. The method of claim 2 wherein the alcohol is selected from a group consisting of methanol, ethanol, propanol, isopropanol, butanol, sec-butanol, isobutanol, and tert-butanol.

4. The method of claim 2 wherein the oxidizer is selected from a group consisting of hydrogen peroxide and peracetic acid.

5. The method of claim 2 wherein a nucleophile is potassium hydroxide.

* * * * *